United States Patent [19]

Zimmerman

[11] 4,379,073

[45] Apr. 5, 1983

[54] COMPOSITION FOR WOOD TREATMENT

[76] Inventor: Charles J. Zimmerman, Steep Bank Rd., St. James, N.Y. 11780

[21] Appl. No.: 256,822

[22] Filed: Apr. 23, 1981

[51] Int. Cl.³ .............................................. B44D 1/16
[52] U.S. Cl. .................................. 252/400 R; 8/402; 8/590
[58] Field of Search ............... 252/400 R; 8/402, 590, 8/500, 588, 94.1 R, 94.13, 94.19 R, 94.25, 94.26

[56] References Cited

U.S. PATENT DOCUMENTS

| | | |
|---|---|---|
| 1,282,355 | 10/1918 | Anderwert et al. ................ 8/402 |
| 2,733,236 | 1/1956 | Toulmin, Jr. ..................... 8/402 |
| 2,772,137 | 11/1956 | Weber ............................. 8/402 |
| 3,839,073 | 10/1974 | Hill ................................. 8/402 |

*Primary Examiner*—John Kight, III
*Assistant Examiner*—Nathan M. Nutter
*Attorney, Agent, or Firm*—Michael I. Kroll

[57] ABSTRACT

A chemical composition is provided for preservation of wood from rot and the elements whereby the final wood is finished to a brown color wherein said brown color is color fast for several years.

3 Claims, No Drawings

COMPOSITION FOR WOOD TREATMENT

BACKGROUND OF THE INVENTION

1. FIELD OF THE INVENTION

The instant invention relates to a wood treatment additive, the additive being mixed with a standard wood preservative whereby the resulting combination will totally penetrate the wood that is to be preserved and will be color fast.

2. DESCRIPTION OF THE PRIOR ART

The prior art is exemplified by wood preservatives which are impregnated into wood for the purpose of inhibiting rot such uses being for fences, fence posts, barns, sheds and alike. The most widely used preservative is known as CCA which is basically cromated copper arsenate. This material is green in color and is typically impregnated into wood under pressure. The processed wood is then fabricated into such items as fences and fence posts and then sold to the consumer.

Often times after the fence is installed the consumer desires to paint the fence and attempts to cover the cromated copper arsenate with paint with the result being that the green color of the cromated copper arsenate always comes through the paint. Accordingly the consumer is unable to paint the treated wood.

Accordingly it is an object of the instant invention to provide a chemical composition that may be combined with the cromated copper arsenate so that the combination will give a brown color to the resultant impregnated wood so that no further treatment, staining or painting is necessary.

A further object of the invention is to provide a wood treatment so that the treated wood may be used directly, without any further treatment for such uses as fences, decks for homes and sidings for buildings, retaining walls and alike.

SUMMARY OF THE INVENTION

In the present invention the disadvantages of the prior art are overcome by providing a chemical wood treatment whereby wood is pressure impregnated with the combination of cromated copper arsenate, 1-amino-8-naphtol-3, 6-Disulfonic acid and brown dye purchased typically as brown acid dye. When this resulting combination is impregnated under pressure into the wood the resulting wood will have a color fast preservative treatment enabling the user to use wood for outdoor use without any additional treatment.

DESCRIPTION OF THE PREFERRED EMBODIMENTS

The instant chemical compounds consists of three materials namely chromated copper arsenate, 1-amino-8-naphthol-3, 6-Disulfonic acid and brown acid dye or other acid dyes.

Cromated copper arsenate consists of sodium dichromate or chromium trioxide, copper oxide or copper sulfate and arsenic pentoxide or arsenic acid said sodium dichromate or chromium trioxide and copper oxide or copper sulfate giving the cromated copper arsenate its green color and it is this green color that always penetrates any color paint. Cromated copper arsenate is commercially available in liquid form, and is easily combined with the other two substances which will be described hereinafter.

The second chemical is 1-amino-8-naphthol-3, 6-Disulfonic acid and is typically referred to as H-Acid. Said chemical is a naphthalene derivative and is available in powder form. It has a bulk density of 0.5 kilograms per liter and is soluble. Said material is odorless and has a faintly yellowish color and as of now was used only in the pharmaceutical industry.

The third chemical is an acid dye and is a brown dye which is typically used to dye leather goods.

The instant invention consists of a formula using the three aforementioned chemicals in the following concentrations: Three pounds of 1-amino-8-naphthol-3, 6-Disulfonic acid is combined with 9 pounds of brown acid dye which is added to 1,000 gallons of 2.5% or less of chronated copper arsenate. The resulting chemical is brown in color and is used to pressure treat wood.

The resulting chemical composition stops the oxidization that necessarily takes place when cromated copper arsenate was used by itself. Said oxidation takes place when the chrome in said cromated copper arsenate acts as an oxidizing agent for the copper the result of which causes the green color. The green color could not be eliminated by adding dye to the cromated copper arsenate as the dye could not inhibit the oxidization.

The instant invention stops the oxidization and concurrently adds color to the wood preservative in that the 1-amino-8-naphthol-3, 6-Disulfonic acid surrounds the copper in the chromated copper arsenate so that the chromium is unable to react with the copper and accordingly the solution will stay brown from the effects of an acid dye which is a brown dye.

Not all dyes will work as well as plain dye but as far as brown acid dye and dyes such as C I acid brown 105 dye may be used is concerned the final product is capable of giving a long lasting brown color to wood that will be color fast in excess of six years.

While the chemical composition herein described constitutes a preferred embodiment of the invention, it is understood that the invention is not limited to this precise chemical composition and that changes may be made therein without departing from the scope of this invention.

Having regard to the foregoing disclosure the following is claimed as the inventive and patentable embodiments thereof:

1. A wood preservative for pressure treating wood, said wood preservative comprising:
   (a) chromated copper arsenate;
   (b) 1-amino-8-naphthol-3,6-disulfonic acid;
   (c) brown acid dye; and
   (d) mixing chromated copper arsenate, 1-amino-8-naphthol-3, 6-disulfonic acid and brown acid dye together in the following proportions: Three pounds of 1-amino-8-naphthol-3, 6-disulfonic acid with nine pounds of brown acid dye and 1,000 gallons of 2.5% or less of chromated copper acid.

2. A wood preservative for pressure treating wood, as recited in claim 1, wherein acid dyes of colors other than brown are used.

3. A wood preservative for pressure treating wood, as recited in claim 1, wherein the brown acid dye consists of C I acid brown 105.

* * * * *